(12) United States Patent
Gouriou et al.

(10) Patent No.: US 9,638,462 B2
(45) Date of Patent: May 2, 2017

(54) METHOD FOR PRODUCING A $C_3+$ HYDROCARBON-RICH FRACTION AND A METHANE- AND ETHANE-RICH STREAM FROM A HYDROCARBON-RICH FEED STREAM, AND RELATED FACILITY

(75) Inventors: Julie Gouriou, Rueil Malmaison (FR); Vanessa Gahier, Jouy le Moutier (FR); Sandra Thiebault, Coye-la-Foret (FR); Loic Barthe, Paris (FR)

(73) Assignee: Technip France, Courbevoie (FR)

( * ) Notice: Subject to any disclaimer, the term of this patent is extended or adjusted under 35 U.S.C. 154(b) by 780 days.

(21) Appl. No.: 13/978,183

(22) PCT Filed: Jan. 6, 2012

(86) PCT No.: PCT/EP2012/050162
§ 371 (c)(1),
(2), (4) Date: Sep. 5, 2013

(87) PCT Pub. No.: WO2012/093164
PCT Pub. Date: Jul. 12, 2012

(65) Prior Publication Data
US 2013/0340473 A1    Dec. 26, 2013

(30) Foreign Application Priority Data

Jan. 6, 2011 (FR) .................................... 11 50096

(51) Int. Cl.
*F25J 1/00* (2006.01)
*C07C 7/09* (2006.01)
(Continued)

(52) U.S. Cl.
CPC ............ *F25J 1/0022* (2013.01); *C07C 7/005* (2013.01); *C07C 7/04* (2013.01); *C07C 7/09* (2013.01);
(Continued)

(58) Field of Classification Search
CPC ........ F25J 3/0209; F25J 3/0233; F25J 3/0238; F25J 3/0242; F25J 3/0247; F25J 2240/02;
(Continued)

(56) References Cited

U.S. PATENT DOCUMENTS 4,690,702 A 9/1987 Paradowski et al.
4,889,545 A 12/1989 Campbell et al.
(Continued)

FOREIGN PATENT DOCUMENTS

FR          2 879 729          6/2006
FR            2879729 A1 *    6/2006 ............. F25J 3/0209
WO    WO 2012/093164 A1      7/2012

OTHER PUBLICATIONS

Translation of FR 2879729 A1.*

*Primary Examiner* — Frantz Jules
*Assistant Examiner* — Brian King
(74) *Attorney, Agent, or Firm* — Locke Lord LLP; Alan B. Clement; Peter J. Fallon

(57) ABSTRACT

The method according to the invention comprises the separation of a feed stream (16) into a first fraction (60) and a second fraction (62) and the injection of at least part of the second fraction (62) into a second dynamic expansion turbine (46) to form a second expanded fraction (80).

It comprises the cooling of the second expanded fraction (80) through heat exchange with at least part of the first headstream (84) coming from a first column (28) and the formation of a second feed stream (82) of the first column (28) from the second cooled expanded fraction.

20 Claims, 7 Drawing Sheets

(51) Int. Cl.
*C10G 5/06* (2006.01)
*F25J 3/02* (2006.01)
*C07C 7/00* (2006.01)
*C07C 7/04* (2006.01)

(52) U.S. Cl.
CPC .............. *C10G 5/06* (2013.01); *F25J 3/0209* (2013.01); *F25J 3/0233* (2013.01); *F25J 3/0242* (2013.01); *F25J 2200/04* (2013.01); *F25J 2200/08* (2013.01); *F25J 2200/74* (2013.01); *F25J 2200/78* (2013.01); *F25J 2205/04* (2013.01); *F25J 2210/06* (2013.01); *F25J 2230/24* (2013.01); *F25J 2230/32* (2013.01); *F25J 2230/60* (2013.01); *F25J 2235/60* (2013.01); *F25J 2240/02* (2013.01); *F25J 2245/02* (2013.01); *F25J 2270/04* (2013.01); *F25J 2290/80* (2013.01)

(58) Field of Classification Search
CPC ... F25J 2245/02; F25J 2240/30; F25J 2240/04
See application file for complete search history.

(56) References Cited

U.S. PATENT DOCUMENTS

| | | |
|---|---|---|
| 6,244,070 B1 | 6/2001 | Lee et al. |
| 6,526,777 B1 | 3/2003 | Campbell et al. |
| 2005/0204774 A1 | 9/2005 | Foglietta et al. |
| 2006/0144081 A1* | 7/2006 | Paradowski ........... F25J 3/0209 62/620 |
| 2010/0011809 A1* | 1/2010 | Mak ....................... F25J 3/0209 62/620 |
| 2010/0263407 A1* | 10/2010 | Paradowski ........... F25J 3/0209 62/621 |
| 2011/0005273 A1* | 1/2011 | Gahier .................. F25J 3/0209 62/621 |
| 2012/0000245 A1* | 1/2012 | Currence ............... F25J 3/0209 62/620 |

\* cited by examiner

METHOD FOR PRODUCING A C$_3$+ HYDROCARBON-RICH FRACTION AND A METHANE- AND ETHANE-RICH STREAM FROM A HYDROCARBON-RICH FEED STREAM, AND RELATED FACILITY

This application is a National Stage patent application of International Patent Application Number, PCT/EP2012/050162, filed on Jan. 6, 2012, which claims priority to FR 11 50096, filed on Jan. 6, 2011.

The present invention relates to a method for producing a C$_3^+$ hydrocarbon-rich cut and a methane- and ethane-rich stream, from a feed stream containing hydrocarbons, the method comprising the following steps:

partially cooling and condensing a first fraction of the feed stream in a first heat exchanger;

injecting the first cooled fraction into a first separating flask to form a first gas headstream and a first liquid bottoms stream;

injecting at least part of the first headstream into a first dynamic expansion turbine;

forming a first feed stream of a first column from the first expanded fraction coming from the first dynamic expansion turbine and injecting the first feed stream into the lower part of a first column to recover a first headstream and a first bottoms stream;

heating at least part of the first headstream in a second heat exchanger, then in the first heat exchanger, and compressing at least part of the heated headstream in a first compressor coupled to the first turbine, then in a second compressor to form the methane- and ethane-rich stream;

injecting the first bottoms stream into a second fractionating column to recover a second headstream and a second bottoms stream;

forming the C$_3^+$ hydrocarbon-rich cut from the second bottoms stream;

at least partially cooling and condensing the second headstream, advantageously in the first heat exchanger, and injecting the second partially condensed headstream into a head separating flask to form a second gas headstream and a second liquid bottoms stream;

injecting the second liquid bottoms stream in reflux into the second fractionating column;

at least partially cooling and condensing the second gas headstream, advantageously in the second heat exchanger;

expanding the second partially condensed headstream and injecting into the first column;

injecting at least part of the first bottoms stream into the first column and/or into the second fractionating column.

Such a method is intended to extract a C$_3^+$ cut, in particular comprising propylene, propane and heavier hydrocarbons, in particular from a natural feed gas, refinery gas, or synthetic gas stream obtained from other hydrocarbonaceous sources such as coal, raw oil or naphtha.

Natural gas generally contains a majority of methane and ethane making up at least 50% of the gas. It also contains a more negligible quantity of heavier hydrocarbons, such as propane or butane. In certain cases, it also contains helium, hydrogen, nitrogen and carbon dioxide.

The method according to the invention is advantageously intended for the recovery of propane and heavier hydrocarbons from natural gas.

These heavy hydrocarbons, and in particular butane and propane, can be marketed and therefore have an economic value. In this respect, the demand for natural gas liquids as filler for the petrochemical industry is increasing steadily and should continue to increase in the years to come.

Furthermore, for method reasons, it is necessary to separate the heavy hydrocarbons, so as to prevent them from condensing during transport and/or handling of the gases. This makes it possible to avoid incidents such as the occurrence of liquid plugs in the transport or treatment equipment designed for gas effluents.

To recover the liquids from the natural gas, it is known to use an oil absorption method that makes it possible to recover approximately 75% of the butanes and 85 to 90% of the pentanes and heavier hydrocarbons.

This method is improved by the use of refrigerated oil. In that case, the propane extraction level can be above 90%.

To achieve higher recovery rates, a cryogenic expansion method must be used.

Traditionally in this type of method, the gaseous feed is cooled, and is partially condensed in a gas/gas heat exchanger.

The feed is then separated in a separating flask. Then, the liquid part is treated in a traditional fractionating column and the vapor effluent of the separator feeds a thermal expansion turbine or a valve, to be sent, after expansion, into the fractionating column.

In the cryogenic method, the temperature is lowered to approximately −90° C. To cool the gas to such temperatures, it is known to use outside refrigerants, a dynamic expansion turbine, or a combination of the two. Such a method has the advantage of being easy to start and offering satisfactory operating flexibility.

A method of the aforementioned type is for example described in U.S. Pat. No. 4,690,702. Such a method is particularly effective to offer good recovery of the C$_3^+$ hydrocarbons. It is, however, desired to improve the energy efficiency of the method.

One aim of the invention is to obtain a method for producing a C$_3^+$ hydrocarbon-rich cut from a feed stream, extremely economically, with a low bulk, and more efficiently than in the known methods.

To that end, the invention relates to a method of the aforementioned type, characterized in that it comprises the following steps:

separating the feed stream into the first fraction of the feed stream and a second fraction of the feed stream;

injecting at least part of the second fraction of the feed stream into a second dynamic expansion turbine to form a second expanded fraction;

cooling at least part of the second expanded fraction by heat exchange with at least part of the first headstream coming from the first column;

forming a second feed stream of the first column from the second cooled expanded fraction; and injecting the second feed stream into the first column.

The method according to the invention may comprise one or more of the following features, considered alone or according to all technically possible combinations:

the second expanded fraction coming from the second dynamic expansion turbine is put in a heat exchange relationship with at least part of the second headstream, advantageously in the second heat exchanger;

at least part of the first expanded fraction coming from the first turbine is cooled by heat exchange with at least part of the first headstream, advantageously in the second heat exchanger, before injection into the first column;

the second fraction of the feed stream is cooled and is partially condensed advantageously in the first heat exchanger, the second cooled and partially condensed fraction being injected into a second separating flask, the third headstream coming from the second separating flask being at least partially injected into the second dynamic expansion turbine;

the third bottoms stream coming from the separating flask is expanded, and is heated, advantageously in the first heat exchanger, then is injected into the first column and/or into the second fractionating column;

a fraction coming from the first bottoms stream recovered from the first separating flask is injected into a liquid stream formed from the second fraction of the feed stream;

the method comprises the following steps:
expansion, heating, and partial evaporation of the first bottoms stream coming from the first separating flask;
injection of the first bottoms stream into a downstream separating flask to form a fourth bottoms stream and a fourth headstream, the fourth headstream being cooled, advantageously in the second heat exchanger, then being injected into the first column to form a second auxiliary feed stream;

the method comprises the following steps:
injecting the second expanded fraction coming from the second dynamic expansion turbine into an auxiliary downstream separating flask to form a fifth gas headstream and a fifth liquid bottoms stream;
cooling the fifth gas headstream and injecting into the first column;
injecting the fifth liquid bottoms stream into the first column and/or into the second column;

the first bottoms stream coming from the first separating flask is heated in the first heat exchanger, before being injected into the second fractionating column;

the method comprises the following steps:
separating the first headstream into a first turbine feed fraction, conveyed up to the first dynamic expansion turbine, and a column feed fraction that is injected into the second heat exchanger to form an auxiliary column feed stream;
injecting the auxiliary column feed stream into the first column;

the method comprises the following steps:
removing, in the first headstream, a secondary recompression fraction upstream of the first compressor;
passage of the secondary recompression fraction into a third compressor coupled to the second dynamic expansion turbine;
injecting the secondary compressed recompression fraction coming from the third compressor into the first heated headstream downstream of the first compressor;
the second compressor comprises a first compression stage, at least one second compression stage and a refrigerant inserted between the first compression stage and the second compression stage, the method comprising a step for the passage of the first compressed overhead stream coming from the first compressor successively in the first compression stage, the refrigerant, then the second compression stage;

the method comprises the following steps:
injecting at least part of the second expanded fraction coming from the second dynamic expansion turbine into an auxiliary column;
recovering a third bottoms stream coming from the auxiliary column,
forming the second column feed stream from the third auxiliary column bottoms stream;

the method comprises the following steps:
separating the feed stream into the first fraction of the feed stream, the second fraction of the feed stream, and a third fraction of the feed stream;
cooling the third fraction of the feed stream by heat exchange with at least part of the first headstream coming from the first column, advantageously in an upstream heat exchanger separate from the second heat exchanger, and
mixing the third fraction of the cooled feed stream in the first fraction of the cooled feed stream, before passage in the first separating flask;

the method comprises the following steps:
passage of the first headstream into the first heat exchanger;
removal of an auxiliary expansion stream in the first headstream, after its passage in the first heat exchanger;
dynamic expansion of the auxiliary expansion stream in an auxiliary dynamic expansion turbine;
injection of the expanded stream coming from the auxiliary dynamic expansion turbine into the first headstream, before its passage in the first heat exchanger;

the method comprises the following steps:
removing a recirculation stream in the first headstream or in a stream formed from the first headstream;
expansion and injection of the expanded recirculation stream in a stream circulating upstream of the first dynamic expansion turbine, advantageously in the first fraction of the first cooled feed stream or in the first turbine feed stream;

the method comprises pumping the first bottoms stream and heating the first bottoms stream in the first heat exchanger before it is injected into the second fractionating column.

The invention also relates to equipment for producing a $C_3^+$ hydrocarbon-rich cut and a methane-rich stream, from a feed stream containing hydrocarbons, the equipment comprising:

a first heat exchanger to partially cool and condense a first fraction of the feed stream;

a first separating flask and means for injecting the first cooled fraction into the first separating flask to form a first gas headstream and a first liquid bottoms stream;

a first dynamic expansion turbine and means for injecting at least part of the first headstream into the first dynamic expansion turbine;

a first column;

means for forming a first feed stream of the first column from the first expanded fraction coming from the first dynamic expansion turbine and means for injecting the first feed stream into the lower part of the first column to recover a first headstream and a first bottoms stream;

a second heat exchanger for heating at least part of the first headstream; and a first compressor coupled to the first dynamic expansion turbine and a second compressor to compress the heated headstream so as to form the methane-rich stream;

a second fractionating column and means for injecting at least part of the first bottoms stream into the second fractionating column to recover a second headstream and a second bottoms stream;

means for forming the $C_3^+$ hydrocarbon-rich cut from the second bottoms stream;

means for at least partially cooling and condensing the second headstream, advantageously comprising the first heat exchanger;

a head separating flask and means for injecting the second partially condensed headstream into the head separating flask to form a second gas headstream and a second liquid bottoms stream;

means for injecting the second liquid bottoms stream in reflux into the second fractionating column;

means for partially cooling and condensing the second headstream, advantageously in the second exchanger;

means for expanding the second partially condensed headstream and means for injecting into the first column in reflux;

means for injecting at least part of the first bottoms stream into the first column and/or into the second fractionating column;

characterized in that the equipment comprises:

means for separating the feed stream into a first fraction of the feed stream and a second fraction of the feed stream;

a second dynamic expansion turbine and means for injecting at least part of the second fraction of the feed stream into the second dynamic expansion turbine to form a second expanded fraction;

means for cooling at least part of the second expanded fraction by heat exchange with at least part of the first headstream coming from the first column;

means for forming a second feed stream of the first column from the second cooled expansion fraction; and means for injecting the second feed stream into the first column.

The equipment according to the invention may comprise one or more of the following features, considered alone or according to all technically possible combinations:

an auxiliary column;

means for injecting at least part of the second expanded fraction coming from the second dynamic expansion turbine into the auxiliary column, to recover a third bottoms stream coming from the auxiliary column;

means for forming the second feed stream of the first column from the third bottoms stream coming from the auxiliary column.

The invention will be better understood upon reading the following description, provided solely as an example and done in reference to the appended drawings, in which.

In all of the following, the same references will be used to designate a stream circulating in a pipe and the pipe that conveys it.

Furthermore, unless otherwise indicated, the percentages cited are molar percentages, and the pressures given are in absolute bars.

In the digitally simulated examples, the output of each compressor is chosen as being 82% polytropic and the output of each turbine is 85% adiabatic.

Likewise, the distillation columns described use plates, but they can also use bulk or structured trim. A combination of plates and trim is also possible.

The additional turbines described drive compressors, but they can also drive variable-frequency electric generators whereof the electricity produced can be used in the network via a frequency converter.

The streams whereof the temperature is higher than the ambient temperature are described as being cooled by aero-refrigerants. Alternatively, it is possible to use water exchangers, for example using fresh water or seawater.

Figure 1:
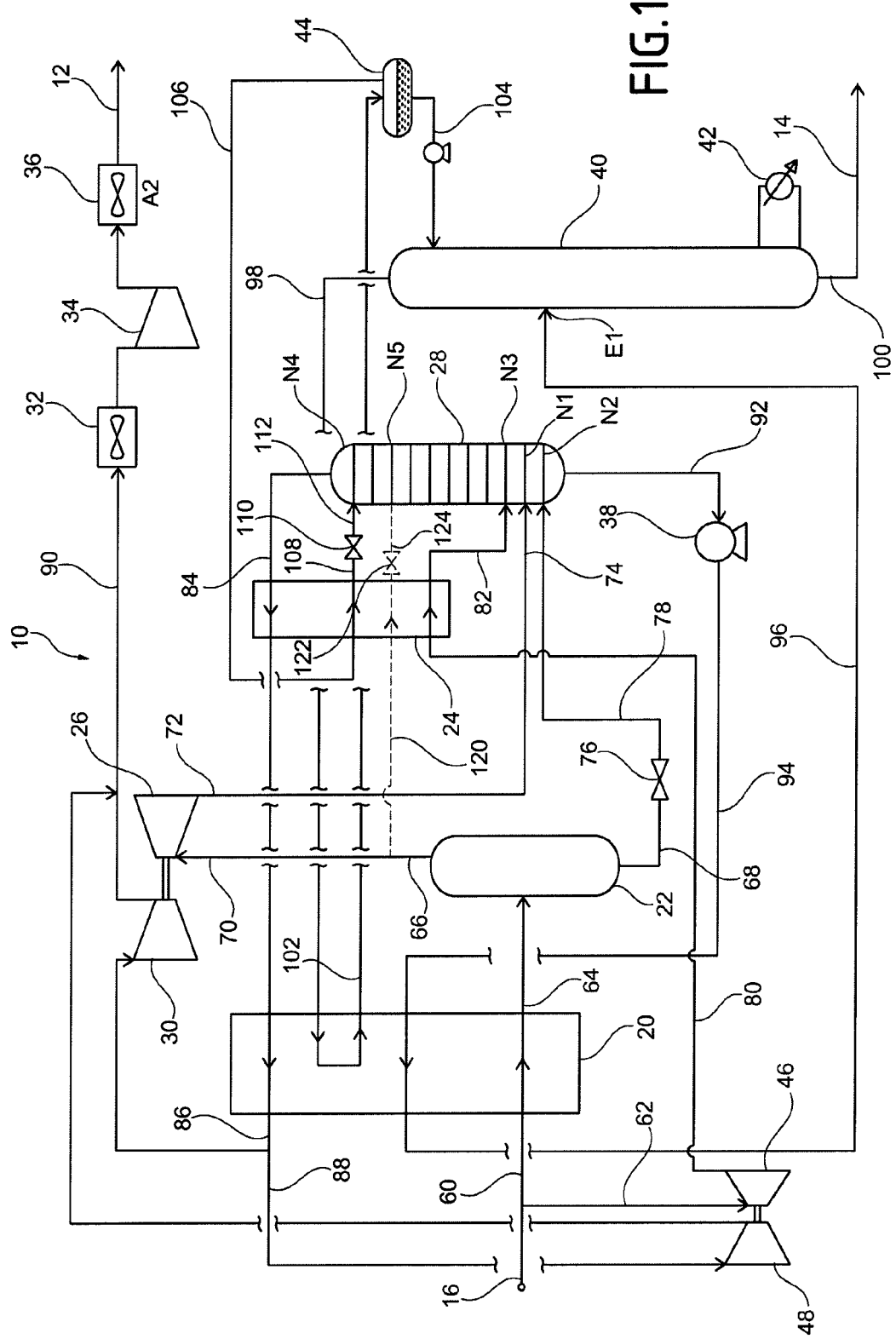
FIG. 1 is a summary flowchart of a first piece of equipment intended to implement a first method according to the invention.

A first piece of equipment 10 according to the invention is shown in FIG. 1. This equipment is intended to produce a methane- and ethane-rich stream 12, and a $C_3^+$ hydrocarbon-rich stream 14 from a gas feed stream 16.

The method and equipment 10 advantageously apply to the construction of a new $C_3^+$ hydrocarbon recovery unit.

The equipment 10 comprises, from upstream to downstream, a first heat exchanger 20, a first separating flask 22, a second heat exchanger 24, and a first dynamic expansion turbine 26.

The equipment 10 also comprises a first column 28, a first compressor 30 coupled to the first dynamic expansion turbine 26, a first air refrigerant 32, a second compressor 34 and a second air refrigerant 36.

The equipment 10 also comprises a first pump 38 situated downstream of the first column 28 and a second fractionating column 40 provided with a reboiler 42 and a head separating flask 44.

According to the invention, the equipment 10 also comprises a second dynamic expansion turbine 46, separate from the first dynamic expansion turbine 26, and a third compressor 48 coupled to the second dynamic expansion turbine 46.

A first production method according to the invention, implemented in the equipment 10, will now be described.

The gas feed stream 16 is a natural gas stream, a refinery gas stream, or a synthetic gas stream obtained from a hydrocarbonaceous source such as coal, raw oil, or naphtha.

In the example illustrated in the figures, the stream 16 is a dehydrated natural gas stream. It advantageously contains less than 1 ppm of water.

The feed stream 16 generally has between 2% and 15% by moles of $C_3^+$ hydrocarbons to be extracted and between 75 and 95% by moles of methane and ethane.

In one particular example, the feed stream 16 is formed from a dehydrated natural gas that comprises, by moles, 1.80% nitrogen, 89.61% methane, 4.38% ethane, 2.52% propane, 0.35% isobutane, 0.75% n-butane, 0.12% isopentane, 0.12% n-pentane, 0.15% n-hexane, 0.15% n-heptane, and 0.01% carbon dioxide.

The feed stream 16 has a pressure greater than 35 bars, in particular greater than 50 bars, and a temperature close to the ambient temperature, and in particular comprised between 30° C. and 50° C., for example substantially equal to 40° C.

In reference to FIG. 1, the feed stream 16 is first divided into a first fraction 60 of the feed stream and a second fraction 62 of the feed stream.

The ratio of the molar flow rate of the first fraction 60 to the second fraction 62 is for example greater than 2 and is in particular comprised between 2 and 15.

In the illustrated example, the first fraction 60 is first injected into the first heat exchanger 20, where it is cooled and partially condensed to form a first fraction 64 of the first cooled feed stream.

The temperature of the first cooled feed stream fraction 64 is below −10° C. and in particular equal to −45.1° C. The first fraction 64 is then injected into the first separating flask 22. The liquid content of the first feed fraction 64 is advantageously less than 50% molar.

A first gas headstream 66 and a first liquid bottoms stream 68 are extracted from the first separating flask 22.

In this example, the entire first gas headstream 66 forms a turbine feed fraction 70 that is injected into the first dynamic expansion turbine 26.

The turbine feed fraction 70 is expanded in the first turbine 26 up to a pressure substantially equal to the operating pressure of the column 28. This pressure is below 40 bars, and in particular comprised between 10 bars and 30 bars, while advantageously being equal to approximately 24 bars.

The temperature of the first expanded fraction 72 coming from the first dynamic expansion turbine 26 is below −30° C. and is in particular equal to −77.9°.

In this example, the entire first expanded fraction 72 forms a first feed stream 74 of the column 28 that is injected directly at a level N1 lower than the first fractionating column 28, without passing through a heat exchanger.

The lower part of the column 28 is situated at a height of less than 40% of the height of the column 28.

Thus, the level N1 is for example situated at the thirteenth stage starting from the top of the column 28.

The first bottoms stream 68 is expanded in a first static expansion valve 76 to form an expanded bottoms stream 78.

The expanded bottoms stream 78 has a pressure substantially equal to the operating pressure of the column 28 and a temperature below −20° C. and in particular substantially equal to −59.8° C.

The first expanded bottoms stream 78 is injected into the column 28 at a level N2 situated below the level N1, at the base of the column 28.

In this example, the entire second fraction 62 of the feed stream is injected into the second dynamic expansion turbine 46.

The second fraction 62 of the feed stream is injected into the turbine 46, without passing through the first heat exchanger 20 in this example. The second fraction 62 thus reaches the second turbine 46 without being put into a heat exchange relationship with another stream circulating in the equipment.

The second fraction 62 of the feed stream is then expanded in the second expansion turbine 46 up to a pressure substantially equal to the pressure of the column 28 or slightly higher than the pressure of the column 28, i.e. greater at most by about 2 bars relative to the pressure of the column 28.

The second expanded fraction 80 coming from the second dynamic expansion turbine 46 is then conveyed in its entirety up to the second heat exchanger 24 to be cooled there and to form a second feed stream 82 of the first column 28.

The temperature of the second feed stream 82 recovered at the outlet of the second heat exchanger 24 is below −40° C. and is in particular substantially equal to −83.1° C.

The second feed stream 82 is injected into the first fractionating column 28 at a level N3 situated in the lower part of the column 28, above the level N1. This level N3 is for example situated at the twelfth stage starting from the top of the column 28.

In this example, the expansion of the first feed fraction 70 in the first dynamic expansion turbine 26 makes it possible to recover 9605 kW of energy, and the expansion of the second fraction 62 makes it possible to recover 1904 kW of energy.

A first headstream 84 is recovered at the head of the first fractionating column 28.

This first headstream 84 is successively heated in the second heat exchanger 24, then in the first heat exchanger 20 to form a first heated headstream 86.

The temperature of the first heated headstream 86 at the outlet of the first exchanger 20 is above 10° C. and is in particular substantially equal to 38° C.

A secondary recompression fraction 88 is removed from the first heated headstream 86, at the outlet of the first exchanger 20.

The ratio of the molar flow rate of the removed secondary recompression fraction 88 relative to the heated headstream 86 coming from the exchanger 20 is less than 20%, and is in particular comprised between 5% and 20%.

The rest of the heated headstream 86 is then injected into the first compressor 30 to be compressed at a pressure greater than 20 bars and in particular substantially equal to 30.2 bars.

The secondary recompression fraction 88 is recompressed in the third compressor 48 coupled to the second dynamic expansion turbine 46, up to a pressure substantially equal to the compression pressure of the rest of the first heated headstream 86 coming from the first compressor 30.

The compressed secondary recompression fraction 88 is then reinjected into the heated headstream coming from the first compressor 30 to form the compressed heated headstream 90.

Then, the compressed heated headstream 90 is injected into the first refrigerant 32, to be cooled substantially to ambient temperature, before being injected into the second compressor 34.

The first compressed fraction 90 is thus compressed to a pressure greater than 40 bars and in particular substantially equal to 51 bars.

The compressed fraction coming from the second compressor 34 is then injected into the second refrigerant 36 to be cooled to a temperature substantially equal to the ambient temperature, for example equal to 40° C., and thus to form the extracted methane- and ethane-rich stream 12 of the method.

The molar content of methane and ethane of the stream 12 is greater than 98% molar.

The stream 12 also comprises more than 99% molar of the methane contained in the feed stream and less than 5% of the $C_3^+$ hydrocarbons contained in the feed stream 16.

The first bottoms stream 92 coming from the column 28 is rich in $C_3^+$ hydrocarbons. It thus comprises more than 40% by moles of $C_3^+$.

The first bottoms stream 92 has a temperature below −30° C. and in particular substantially equal to −70° C.

The bottoms stream 92 is injected into the first pump 38 to be compressed at a pressure greater than 20 bars that substantially corresponds to the operating pressure of the second column 40.

This pressure is for example substantially equal to 29 bars. More generally, this pressure is greater by at least 2 bars than the pressure of the column 28 and is for example comprised between 10 and 35 bars.

The first compressed bottoms stream 94 is then injected into the first heat exchanger 20, advantageously without passing through the second heat exchanger 24, to be heated to a temperature above 0° C., and in particular equal to 11.6° C.

The first heated bottoms stream 96 coming from the first heat exchanger 20 is then injected into the fractionating column 40, at a level E1 corresponding for example to the sixteenth stage starting from the top of the column 40.

The fractionating column 40 produces a second headstream 98 and a second bottoms stream 100.

The second bottoms stream 100 is recovered at a temperature above 50° C. and in particular equal to 99° C. It contains more than 90% by moles, advantageously 98% by moles of the propane contained in the feed stream 16. This stream 100 also comprises more than 50% molar of propane.

In the illustrated example, the stream 100 forms the $C_3^+$ hydrocarbon-rich cut 14. It contains 1.18% ethane, 59.05% propane, 8.28% i-butane, 17.75% n-butane, 2.84% n-pentane, 2.84% i-pentane, 3.55% n-hexane, 4.50% n-heptane.

The second headstream 98 is gaseous. It is recovered at a temperature below 0° C. and in particular substantially equal to −12.9° C.

The second headstream 98 is then injected into the first heat exchanger 20 to be cooled and partially condensed there and to form a second cooled headstream 102.

The second cooled headstream 102 has a temperature below −20° C. and a liquid content above 10% molar.

The second cooled headstream 102 is then injected into the head separating flask 44 to be separated there into a second bottoms stream 104 and a second headstream 106.

The second bottoms stream 104 is liquid. It is pumped in reflux into the second column 40 to be injected therein at a head level for example situated at the first stage relative to the head of the column 40.

The second headstream 106 is injected into the second heat exchanger 24 to be cooled there to a temperature below −40° C. and form a second cooled headstream 108.

The stream 108 is then expanded in a second static expansion valve 110 to form an expanded reflux stream 112 injected into the first column 28 at a pressure substantially equal to the operating pressure of the column 28, at a level N4 situated near the head of that column 28, above the level N3.

Temperature, pressure and molar flow rate examples of the different streams are provided in table 1 below.

| Stream | Temperature (° C.) | Pressure (bara) | Flow rate (kmol/h) |
|---|---|---|---|
| 12 | 40.0 | 51.00 | 47888 |
| 14 | 99.3 | 28.75 | 2112 |
| 16 | 40.0 | 51.00 | 50000 |
| 60 | 40.0 | 51.00 | 45000 |
| 62 | 40.0 | 51.00 | 5000 |
| 64 | −45.1 | 50.50 | 45000 |
| 66 | −45.1 | 50.50 | 42158 |
| 72 | −77.9 | 23.90 | 42158 |
| 78 | −59.8 | 23.90 | 2842 |
| 80 | −1.9 | 24.40 | 5000 |
| 82 | −83.1 | 23.90 | 5000 |
| 84 | −85.1 | 23.70 | 47888 |
| 86 | 38.0 | 23.00 | 47888 |
| 88 | 38.0 | 23.00 | 7922 |
| 90 | 62.2 | 30.24 | 47888 |
| 96 | 11.6 | 28.75 | 4955 |
| 98 | −12.9 | 28.25 | 5019 |
| 102 | −33.1 | 27.75 | 5019 |
| 104 | −33.1 | 27.75 | 2176 |
| 112 | −86.9 | 23.90 | 2843 |

Table 2 below illustrates the power consumed by the compressor 34 as a function of the flow rate of the second fraction 62 sent toward the second turbine 46. The $C_3^+$ recovery is greater than 99.0% molar.

| Column 40 pressure (bara) | Column 28 pressure (bara) | Flow rate toward turbine 46 (kmol/h) | Turbine power 26 (kW) | Turbine power 46 (kW) | Compressor power 34 (kW) |
|---|---|---|---|---|---|
| 28.3 | 24.2 | 0 | 10224 | 0 | 24476 |
| 28.2 | 24.2 | 1000 | 10040 | 372 | 24256 |
| 28.2 | 24.1 | 2000 | 9899 | 746 | 24102 |
| 28.0 | 24.0 | 3000 | 9777 | 1125 | 24020 |
| 27.9 | 23.9 | 4000 | 9691 | 1511 | 23999 |
| 27.8 | 23.7 | 5000 | 9601 | 1904 | 23983 |
| 27.5 | 23.4 | 6000 | 9600 | 2320 | 24170 |

The energy consumption of the first method according to the invention, made up of the drive energy of the second compressor 34, can be considerably decreased to 23983 kW, versus 24476 kW with a method of the state of the art according to U.S. Pat. No. 4,690,702, in which the same load rate to be processed is used and the same $C_3^+$ recovery is achieved.

Relative to the state of the art according to U.S. Pat. No. 4,690,702, the method according to the invention therefore makes it possible to obtain a significant reduction in the consumed power, while preserving a high selectivity for the recovery of the $C_3^+$ cut.

Furthermore, the method according to the invention makes it possible to come closer to the outputs obtained with an optimized method of the state of the art in which the liquids of the separating flask 22 are sent toward the column 40 after heating in the first exchanger 20, for which the energy consumption is 22440 kW.

In one alternative of the diagram of FIG. 1, in which the liquids of the separating flask 22 are sent toward the second column 40, after heating in the first heat exchanger 20, the gain relative to the optimized method of the state of the art is also in the vicinity of 2%.

In another alternative, shown in broken lines in FIG. 1, the first headstream 66 coming from the first separating flask 22 is separated into the first turbine feed fraction 70 and a second column feed fraction 120.

The ratio of the molar flow rate of the second column feed fraction 120 to the first turbine feed fraction 70 is below 50% and is in particular comprised between 10% and 40%.

The second column feed fraction 120 is then injected into the second heat exchanger 24 to be cooled there to a temperature below −40° C., then is expanded to a pressure substantially equal to the pressure of the column 28 by passing through a third static expansion valve 122.

The auxiliary feed stream 124 thus formed is injected into the column 28 at a level N5 situated between the level N4 and the level N3.

This arrangement can be applied to all of the other embodiments described hereafter.

Figure 2:
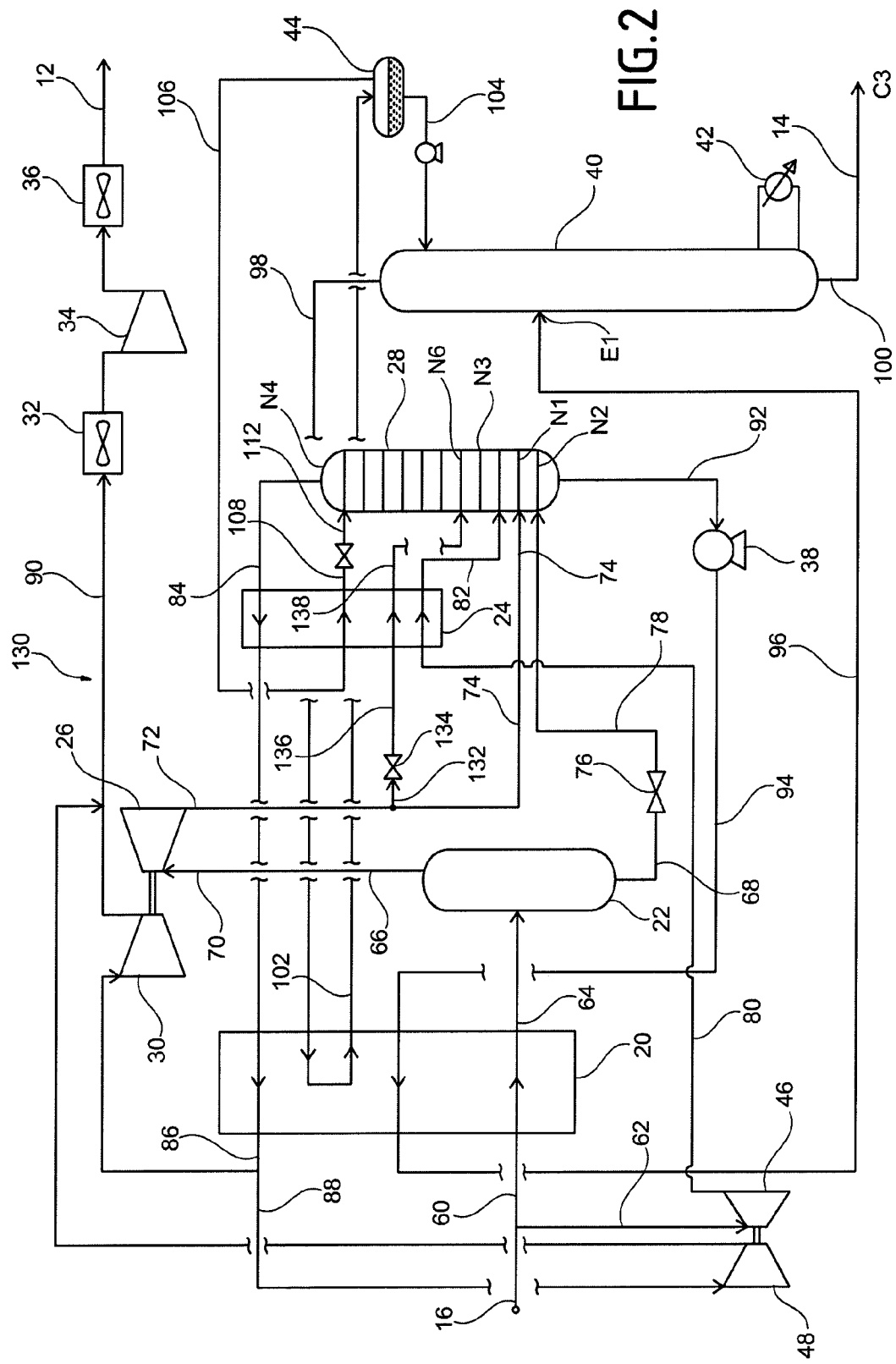
FIG. 2 is a view similar to FIG. 1 of a second piece of equipment intended to implement a second method according to the invention.

A second piece of equipment 130 according to the invention is shown in FIG. 2.

This second equipment 130 is intended to implement a second method according to the invention.

Unlike the first method according to the invention, at least part 132 of the first expanded fraction 72 coming from the first turbine 26 is bypassed through a flow rate control valve 134, to be cooled in the second heat exchanger 24 and to form an additional feed stream 138 of the column 28. A second part of the first fraction 72 forms the second feed stream 74 previously described.

The temperature of the additional feed stream 138 is below −40° C. and is in particular equal to −82.5° C. The additional feed stream 138 is injected into the column 28 at a level N6 situated above the level N3 and below the level N4.

The ratio of the molar flow rate of the additional feed stream 138 to the molar flow rate of the first expanded fraction 72 is less than 70% and is in particular comprised between 1 and 50%.

The second method according to the invention is also similar to the first method according to the invention.

The second method according to the invention makes it possible to further decrease the recompression power by approximately 1.7% relative to the method described in U.S. Pat. No. 4,690,702, and to come closer still to the energy performance obtained in the optimized method of the state of the art described above.

Figure 3:
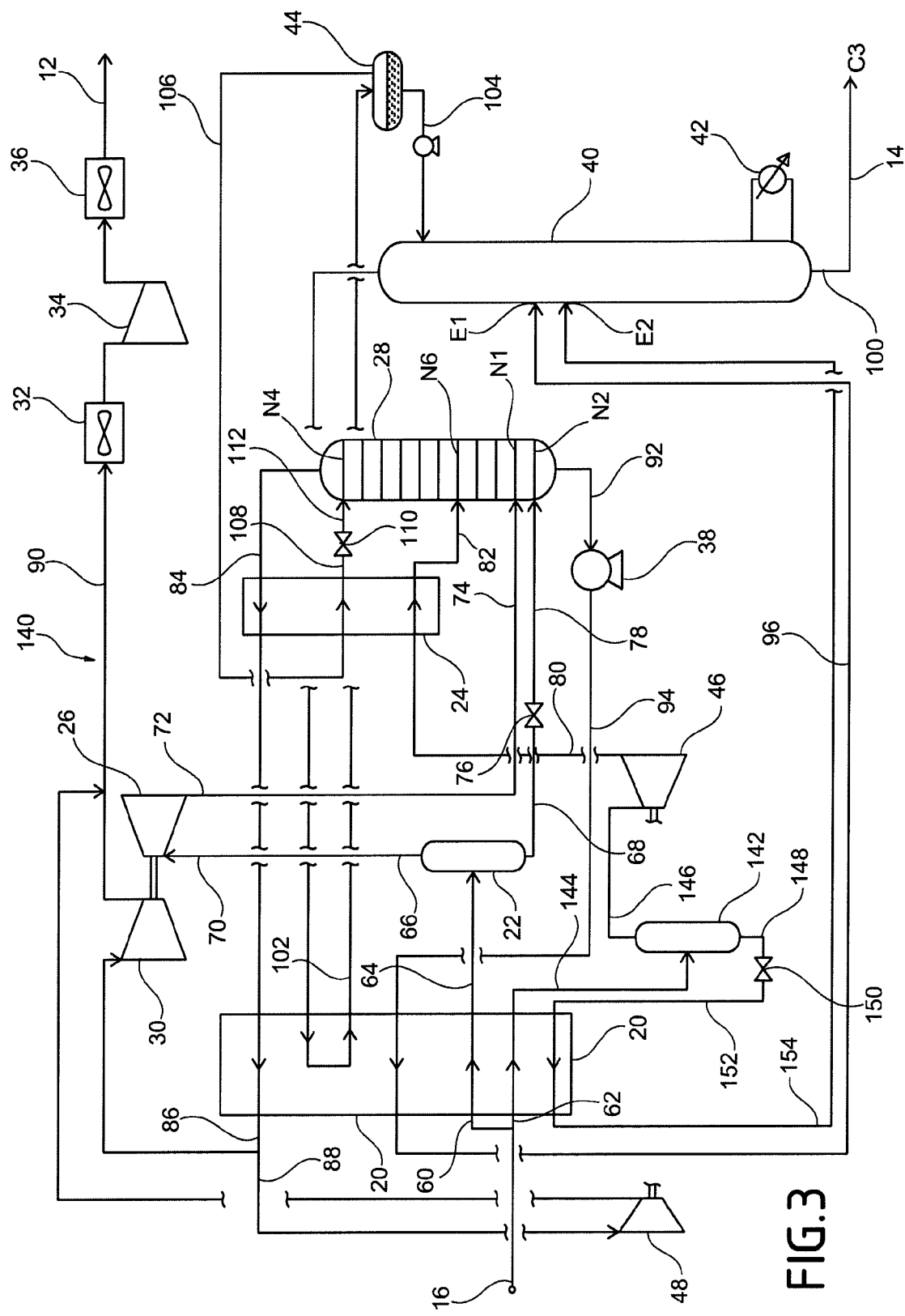
FIG. 3 is a view similar to FIG. 1 of a third piece of equipment intended to implement a third method according to the invention.

A third piece of equipment 140 according to the invention is shown in FIG. 3. Unlike the first piece of equipment 10 according to the invention, the third piece of equipment according to the invention 140 comprises a second separating flask 142 positioned upstream of the second dynamic expansion turbine 46.

Unlike the first method according to the invention, the second fraction of the feed stream 62 is injected into the first heat exchanger 20 to be cooled and partially condensed therein.

The second condensed cooled feed fraction 144 has a temperature below 10° C. and a liquid fraction greater than 1% by moles. The temperature of the second fraction 144 is higher, for example at least 20° C. higher, than the temperature of the first fraction of the cooled feed stream 64 entering the first separating flask 22.

This fraction 144 is injected into the second separating flask 142 to be separated therein into a third headstream 146 and a third bottoms stream 148.

The third headstream 146 makes up the part of the second fraction of the feed stream 62 injected into the second dynamic expansion turbine 46 to form the second expanded fraction 80.

The third bottoms stream 148 is injected into a fourth static expansion valve 150 to be expanded there at a pressure close to the operating pressure of the second column 40 and form a third expanded bottoms stream 152.

The third expanded bottoms stream 152 is then sent into the first heat exchanger 20 be heated therein to a temperature above 0° C. and form a third heated bottoms feed 154.

The third heated bottoms stream 154 is then injected into the second column 40 at a middle level E2 situated below the level E1, for example substantially at level 18 from the head of the column 40.

The implementation of the third method according to the invention is also similar to that of the first method.

Table 3 illustrates the power decrease of the compressor 34 as a function of the feed stream flow rate sent toward the second turbine 142.

| Column 40 pressure (bara) | Column 28 pressure (bara) | Flow rate toward the turbine 46 (kmol/h) | Turbine power 26 (kW) | Turbine power 46 (kW) | Compressor power 34 (kW) |
|---|---|---|---|---|---|
| 28.3 | 24.2 | 0 | 10224 | 0 | 24472 |
| 29.0 | 25.1 | 10000 | 7923 | 2676 | 22204 |
| 29.3 | 25.5 | 15000 | 6861 | 3927 | 21208 |
| 29.5 | 25.8 | 20000 | 5839 | 5187 | 20615 |
| 31.0 | 25.4 | 25000 | 4785 | 6562 | 20688 |
| 31.5 | 25.4 | 26000 | 4541 | 6587 | 20870 |
| 31.9 | 23.3 | 27000 | 4311 | 6878 | 21057 |

The consumed power thus decreases by 15.8% relative to the method described in U.S. Pat. No. 4,690,702 and 8.1% relative to the optimized method of the state of the art described above.

In one alternative of the third method, the second fraction of the feed stream 62 is conveyed directly toward the second separating flask 142, without passing through the first heat exchanger 20, and without being placed in a heat exchange relationship with another stream circulating in the equipment. The implementation of this alternative is also similar to that described for the third method.

In one alternative of the third method, the third expanded bottoms stream 152 can be at least partially sent toward the first column 28.

Figure 4:
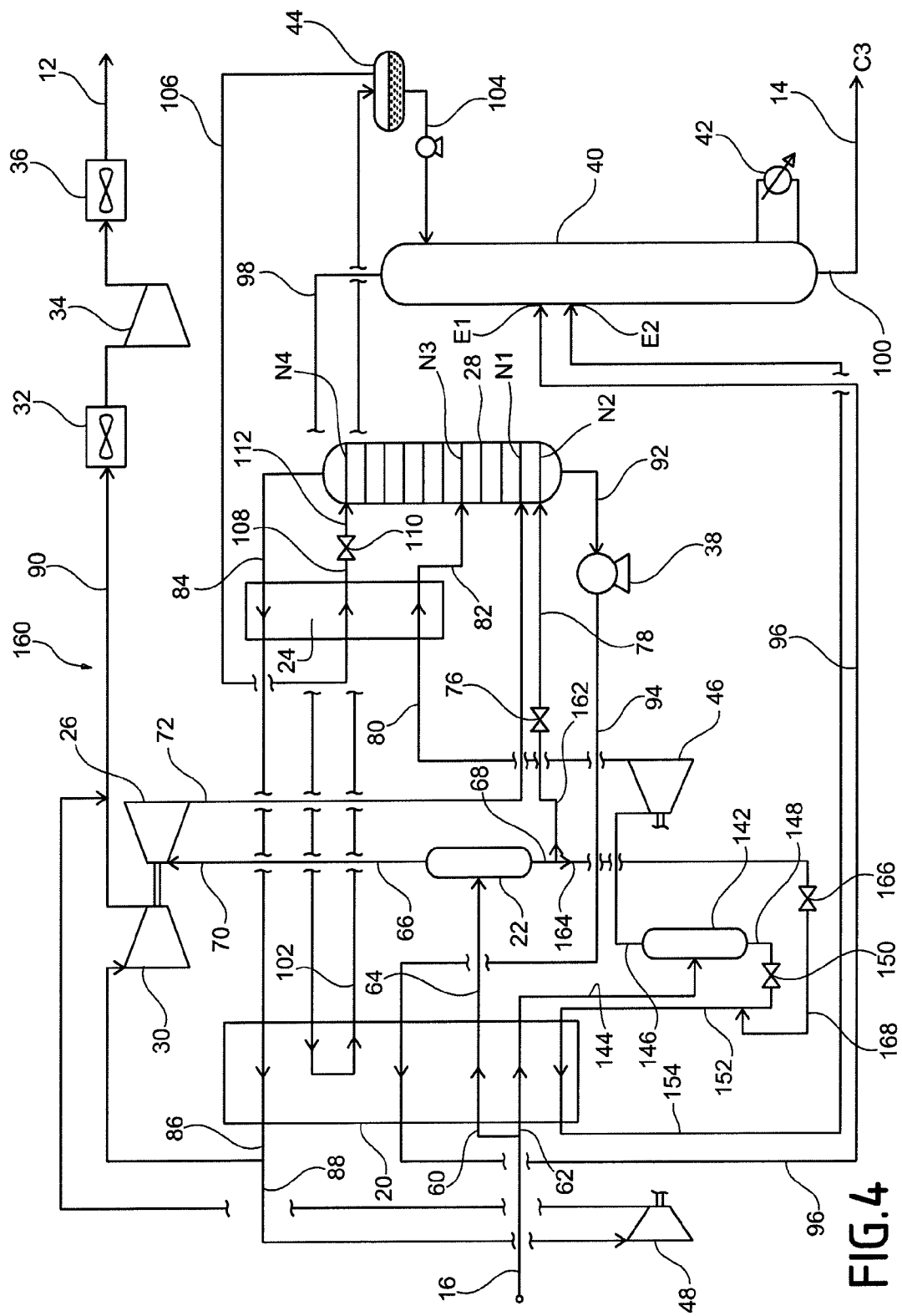
FIG. 4 is a view similar to FIG. 1 of a fourth piece of equipment intended to implement a fourth method according to the invention.

A fourth piece of equipment according to the invention 160 is shown in FIG. 4. This equipment 160 is intended to implement a fourth method according to the invention.

Unlike the third method according to the invention, at least part of the first bottoms stream 68 coming from the first separating flask 22 is injected into a liquid stream formed from the second fraction of the feed stream 62, upstream of the second dynamic expansion turbine 46.

Thus, the first bottoms stream 68 is divided into a first part 162 intended to be expanded in the first static valve 76 to form the first expanded bottoms stream 78.

A second part 164 of the first stream 68 is also injected into a fifth dynamic expansion valve 166 to be expanded therein at a pressure substantially equal to the pressure of the second column 40.

The second expanded part 168 is then injected into the third expanded bottoms stream 152 upstream of the passage of the stream 152 in the first exchanger 20.

The fourth method according to the invention is also implemented similarly to the third method according to the invention.

Figure 5:
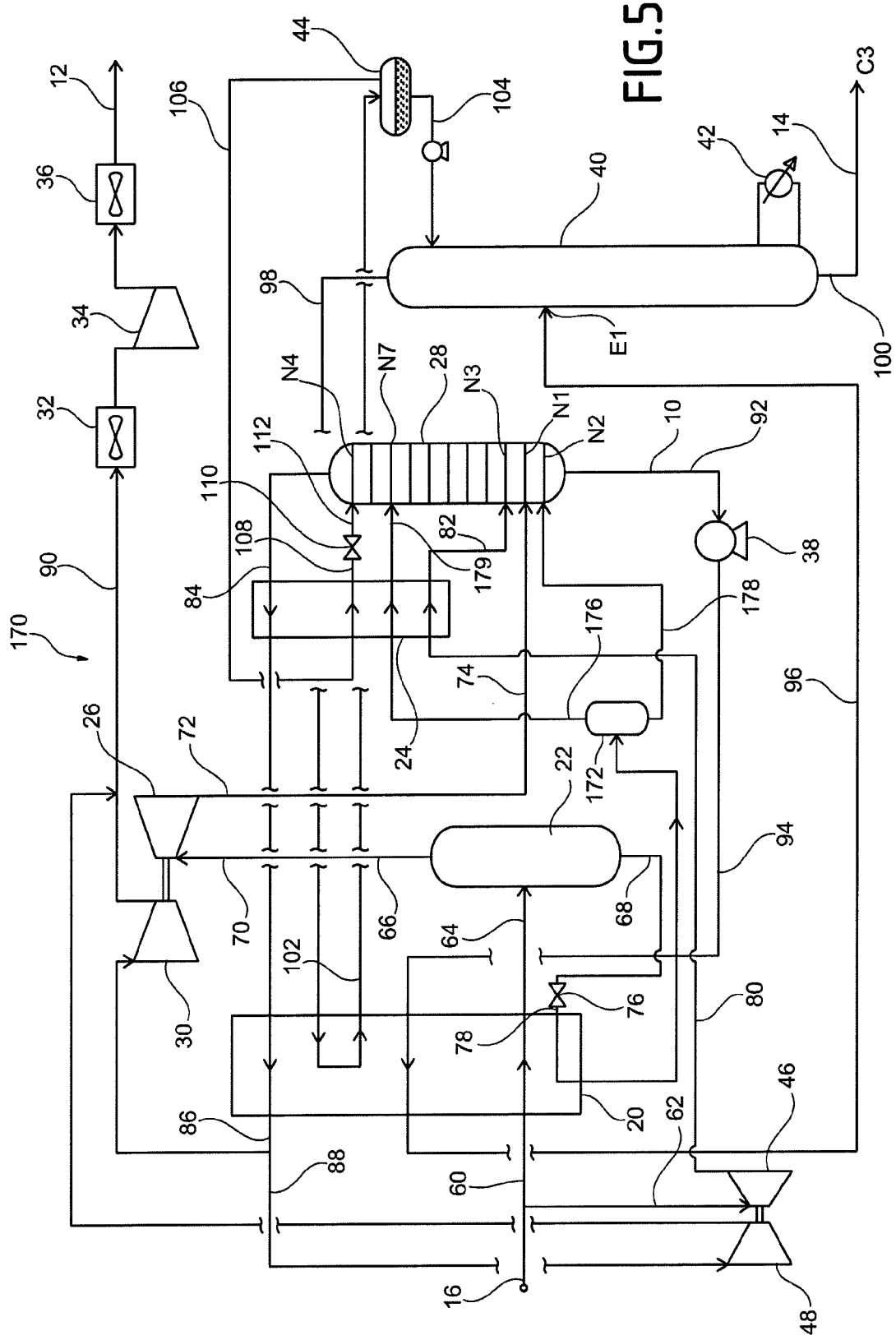
FIG. 5 is a view similar to FIG. 1 of a fifth piece of equipment intended to implement a fifth method according to the invention.

A fifth piece of equipment 170 according to the invention is shown in FIG. 5. This fifth piece of equipment 170 is intended to implement a fifth method according to the invention.

Unlike the first piece of equipment 10, the fifth piece of equipment 170 comprises a downstream separating flask 172 positioned downstream of the first separating flask 22.

As illustrated by FIG. 5, the fifth method according to the invention differs from the first method according to the invention in that the first expanded bottoms stream 78 coming from the valve 76 is injected into the first heat exchanger 20 to be heated and partially evaporated therein to a temperature below 30° C. and advantageously equal to −22° C.

Then, the first cooled bottoms stream 78 coming from the first exchanger 20 is injected into the downstream separating flask 172 to be separated therein into a fourth gas headstream 176 and a fourth liquid bottoms stream 178.

The fourth bottoms stream 178 forms a first auxiliary column feed stream that is injected into a first bottom part of the column 28, for example at level N2.

The fourth gas stream 176 is passed into the second heat exchanger 24 to be cooled and condensed therein and form a second auxiliary column supply stream 179. The stream 179 is injected into the column 28 at a level N7 situated above level N3 and below level N4.

The operation of the fifth method according to the invention is also similar to that of the first method according to the invention.

Alternatively, the liquids coming from the separating flask 172 are sent toward the first column 28 possibly after passing in the second exchanger 24, or in the second column 40, possibly after passage in the second exchanger 24.

Figure 6:
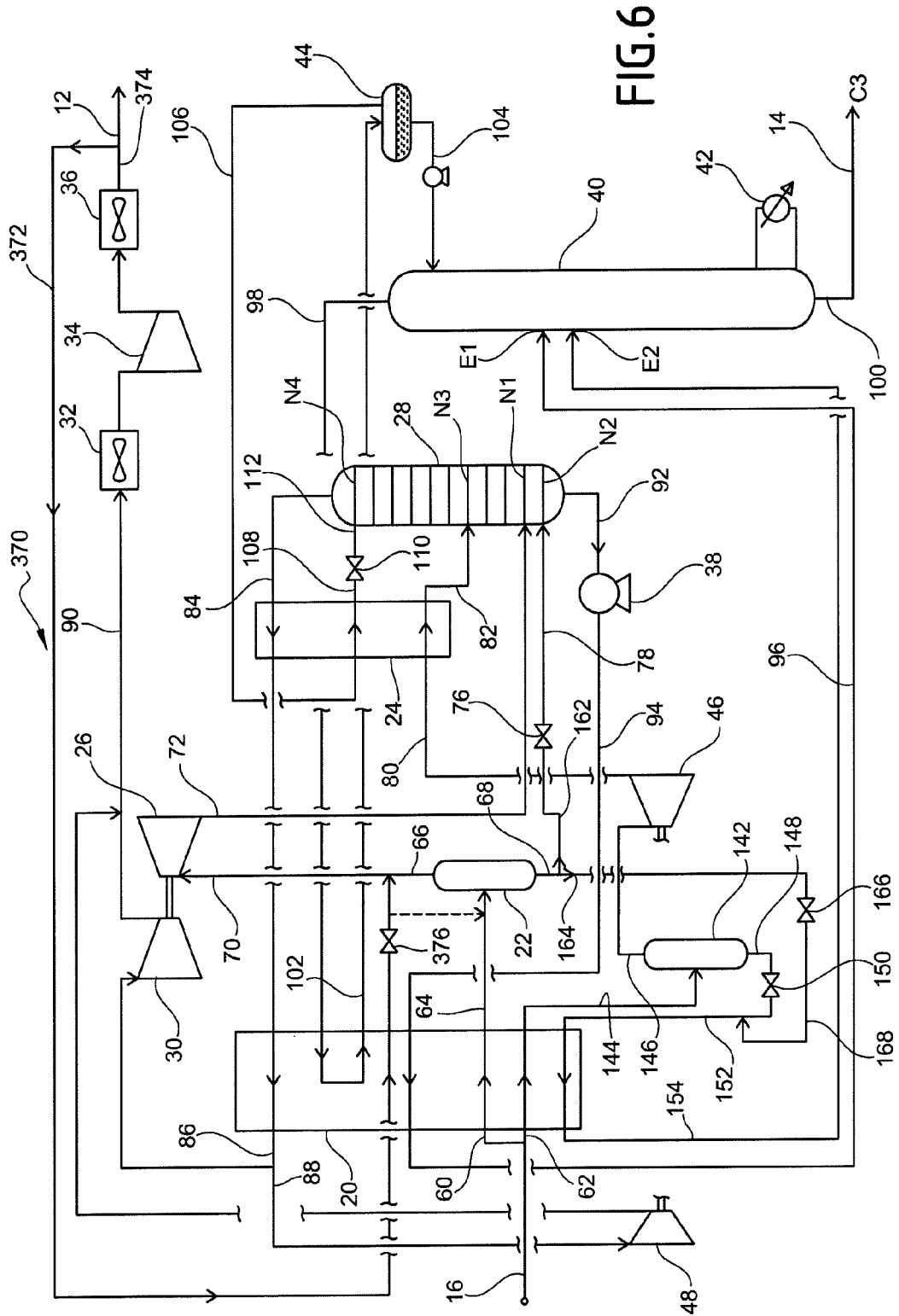
FIG. 6 is a view similar to FIG. 1 of a sixth piece of equipment intended to implement a sixth method according to the invention.

A sixth piece of equipment 370 according to the invention is illustrated in FIG. 6. This sixth piece of equipment 370 is intended to be implemented in a sixth method according to the invention.

The sixth piece of equipment 370 is similar to the fourth piece of equipment 160.

However, unlike the fourth method according to the invention, the sixth method according to the invention comprises the removal of a recirculation stream 372 from the first compressed head fraction 374 coming from the second refrigerant 36, downstream of the second compressor 34.

The ratio of the molar flow rate of the recirculation stream 372 to the molar flow rate of the first compressed head fraction 374 is less than 1%.

The recirculation stream 372 is then cooled in the first heat exchanger 20 to a temperature below 40° C., in particular equal to 25° C.

The recirculation stream 372 is then injected into a stream formed from the first fraction of the feed stream 60, upstream of the first dynamic expansion turbine.

In this example, the recirculation stream 372 is injected into the first stream 66 coming from the first separating flask 22 through a valve 376. In one alternative (not shown), the recirculation stream 372 is injected into the first fraction of the cooled feed stream 64, upstream of the first separating flask 22.

Figure 7:
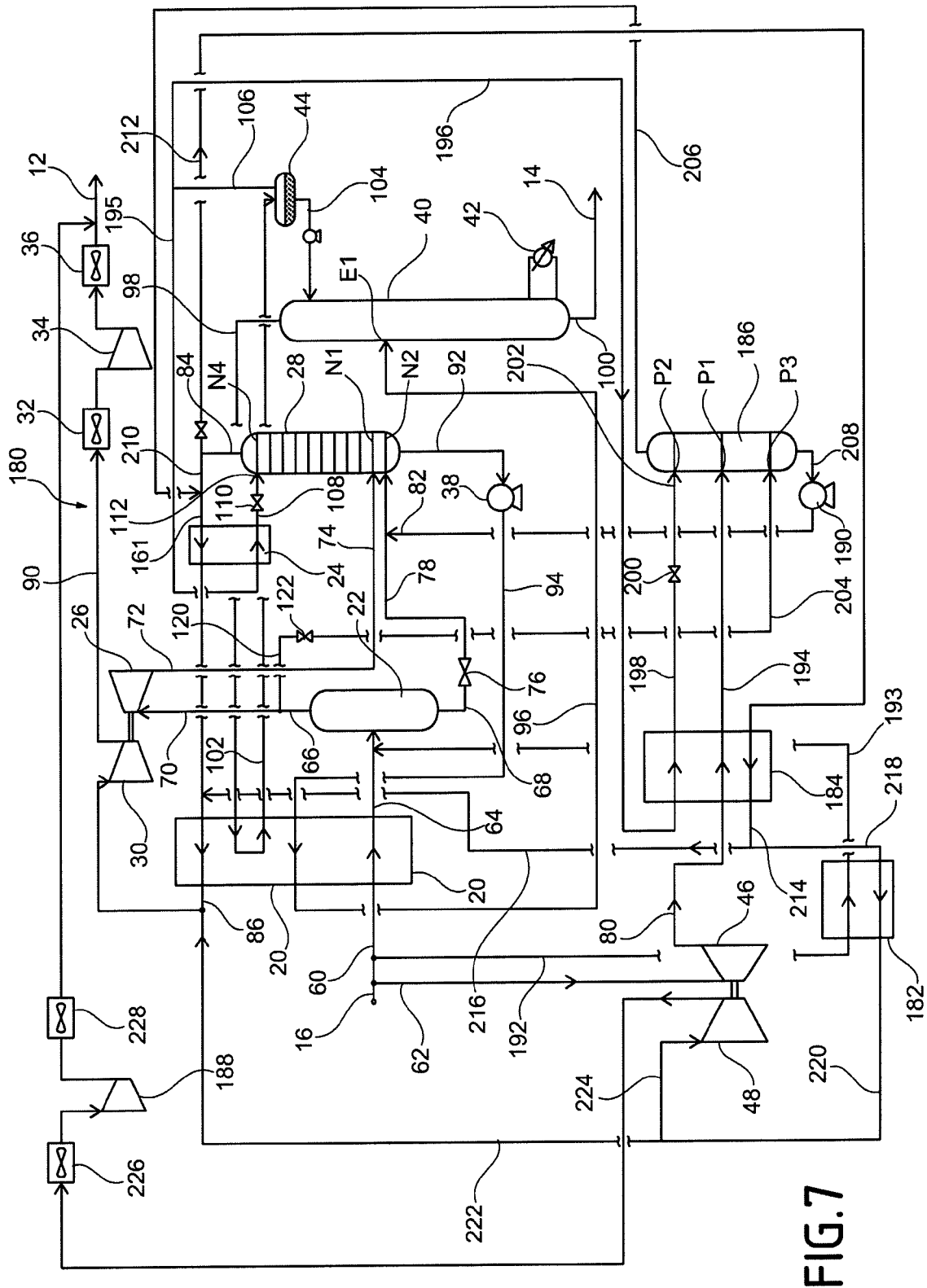
FIG. 7 is a view similar to FIG. 1 of a seventh piece of equipment intended to implement a seventh method according to the invention.

A seventh piece of equipment according to the invention 180 is shown in FIG. 7. This seventh piece of equipment 180 is intended to implement a seventh method according to the invention.

The seventh piece of equipment 180 is advantageously intended to increase the capacity of a piece of equipment of the type described in U.S. Pat. No. 4,690,702.

The existing equipment for example comprises the first heat exchanger 20, the first separating flask 22, the first dynamic expansion turbine 26, the first column 28 and the second fractionating column 40 provided with its head separating flask 44 and the reboiler 42.

The existing equipment also comprises the second compressor 34 and the first compressor 30 coupled to the turbine 26.

As in the equipment 10 shown in FIG. 1, the seventh piece of equipment 180 according to the invention comprises a second dynamic expansion turbine 46 and a third compressor 48 coupled to the second dynamic expansion turbine 46.

Unlike the first equipment 10 according to the invention, the seventh piece of equipment 180 also comprises an upstream heat exchanger 182, a downstream heat exchanger 184, an auxiliary column 186 and an auxiliary compressor 188.

The auxiliary column 186 is provided with an auxiliary bottom pump 190.

The seventh method according to the invention differs from the first method according to the invention in that the feed stream 16 is also separated into a third feed stream fraction 192 that is injected into the upstream heat exchanger 182, in addition to the first fraction 60 and the second fraction 62.

The third cooled fraction 193 coming from the upstream exchanger 182 is reinjected into the first cooled fraction 64 coming from the first heat exchanger 20 upstream of the first separating flask 22.

The ratio of the molar flow rate of the third fraction 192 to the molar flow rate of the feed stream 16 is greater than 5% and is for example below 30%.

Unlike the first method according to the invention, the second expanded fraction 80 coming from the second expansion turbine 46 is injected into the downstream heat exchanger 184 to be cooled therein and to form a first auxiliary feed stream 194 of the auxiliary column 186. The first auxiliary stream 194 is injected into the auxiliary column 186 substantially in the middle part thereof, at an introduction level P1.

The temperature of the first stream 194 is for example below −40° C. and is in particular comprised between −40° C. and −100° C.

The second headstream 106 coming from the head separating flask 44 is separated into a first part 195 and a second part 196.

The first part 195 is conveyed toward the second heat exchanger 24 to form the cooled stream 108, then the expanded reflux stream 112, after expansion in the valve 110.

The second part 196 is conveyed to the downstream heat exchanger 184 to be cooled and partially condensed therein. The second cooled and partially condensed part 198 is then expanded in a seventh static expansion valve 200 to form a second auxiliary feed stream 202 of the auxiliary column 186.

The temperature of the second auxiliary stream 202 is below −40° C. The second auxiliary stream 202 is injected at a head level P2 of the column 186, situated above the level P1.

Unlike the first method according to the invention, and as in the alternative shown in broken lines in FIG. 1, the first headstream 66 is separated into a turbine feed fraction 70 and a second column feed fraction 120.

The second column feed fraction 120 is expanded in the second static expansion valve 122 to form a third auxiliary feed stream 204 of the auxiliary column 186 that is injected at the foot of the column 186 at an introduction level P3 situated below the level P1.

The auxiliary column 186 produces a third gas headstream 206 and a third liquid bottoms stream 208.

The third bottoms stream 208 is pumped by the auxiliary pump 190 to form the second column feed stream 82.

The stream 82 is mixed with the first expanded bottoms stream 78 coming from the first separating flask 22 after expansion in the first valve 76. Thus, the number of injection points in the column 28 remains identical.

In this way, the second column feed stream 82 is formed from the second expanded fraction 80 coming from the second dynamic expansion turbine 46, after passage of that fraction 80 in the auxiliary column 186.

Unlike the first method according to the invention, the first headstream 84 coming from the first column 28 is separated into a first part 210 and a second part 212.

The first part 210 of the first headstream 84 receives the third headstream 206 recovered at the head of the auxiliary column 186, before being injected into the second heat exchanger 24, then in the first heat exchanger 20 to be heated and form the heated headstream 86 therein.

The second part 212 is injected into the downstream heat exchanger 184 to be heated therein.

The second heated part 214 is then separated into a first return stream 216 and a first compression stream 218. The first return stream 216 is reinjected into the first part 210 of the partially heated headstream 84, between the second heat exchanger 24 and the first heat exchanger 20.

The first recompression stream 218 is injected into the upstream exchanger 182 to be heated therein countercurrent to the third fraction of the feed stream 192 up to a temperature above 0° C.

The heated recompression stream 220 recovered at the outlet of the upstream heat exchanger 182 is then separated into a second return stream 222 and a second recompression stream 224.

The second return stream 222 is reinjected into the heated headstream 86 coming from the first heat exchanger 20, upstream of the first compressor 30.

The second recompression stream 224 is injected successively into the third compressor 48, in a first additional refrigerant 226, in the auxiliary compressor 188, then in a second additional refrigerant 228. It is then reinjected downstream of the second compressor 34, in particular while being mixed with the compressed headstream coming from the second refrigerant 36, to form the methane- and ethane-rich stream 12.

The seventh piece of equipment 180 according to the invention therefore makes it possible to significantly increase the flow rate of the feed stream 16, while preserving excellent selectivity for the separation of the $C_3^+$ hydrocarbons, without having to modify the existing installations in the piece of equipment, and in particular the columns 28 and 40, the turbine 26, and the compressors 30 and 34.

In one alternative of the methods previously described, the first expanded bottoms stream 78 is injected after heating into the second fractionating column 40 and not into the first column 28.

In another alternative, the second heat exchanger 24 can be divided into several exchangers, each being fed by part of the first headstream 84 and at least one of the other streams circulating in the heat exchanger 24.

Likewise, the first heat exchanger 20 can also be divided into several exchangers.

In another alternative, an auxiliary expansion stream is removed from the first headstream 86, after its passage in the first heat exchanger 20.

The auxiliary expansion stream is expanded in an auxiliary dynamic expansion turbine separate from the first turbine 26 and the second turbine 46.

Then, the expanded stream coming from the auxiliary dynamic expansion turbine is reinjected into the first headstream, before its passage in the first heat exchanger 20, for example downstream of the second heat exchanger 24.

In another alternative, a propane addition cycle is used to cool certain streams, for example the streams circulating in the first exchanger or in the second exchanger.

The invention claimed is:

1. A method for producing a $C_3^+$ hydrocarbon-rich cut and a methane- and ethane-rich stream, from a feed stream containing hydrocarbons, the method comprising:

partially cooling and condensing a first fraction of the feed stream in a first heat exchanger to form a first cooled fraction;

injecting the first cooled fraction into a first separating flask to form a first gas headstream and a first liquid bottoms stream;

injecting at least part of the first headstream into a first dynamic expansion turbine;

forming a first feed stream of a first column from the first expanded fraction coming from the first dynamic expansion turbine and injecting the first feed stream into the lower part of a first column to recover a first headstream and a first bottoms stream;

heating at least part of the first headstream in a second heat exchanger then in the first heat exchanger, and compressing at least part of the heated headstream in a first compressor coupled to the first turbine, then in a second compressor to form the methane- and ethane-rich stream;

injecting the first bottoms stream into a second fractionating column to recover a second headstream and a second bottoms stream;

forming the $C_3^+$ hydrocarbon-rich cut from the second bottoms stream;

at least partially cooling and condensing the second headstream, advantageously in the first heat exchanger, and injecting the second partially condensed headstream into a head separating flask to form a second gas headstream and a second liquid bottoms stream;

injecting the second liquid bottoms stream in reflux into the second fractionating column;

at least partially cooling and condensing the second gas headstream, advantageously in the second heat exchanger;

expanding the second partially condensed headstream and injecting into the first column;

injecting at least part of the first bottoms stream into the first column and/or into the second fractionating column;

separating the feed stream into the first fraction of the feed stream and a second fraction of the feed stream;

injecting at least part of the second fraction of the feed stream into a second dynamic expansion turbine to form a second expanded fraction;

cooling at least part of the second expanded fraction by heat exchange with at least part of the first headstream coming from the first column;

forming a second feed stream of the first column from the second cooled expanded fraction; and injecting the second feed stream into the first column.

2. The method according to claim 1, wherein the second expanded fraction coming from the second dynamic expansion turbine is put in a heat exchange relationship with at least part of the second headstream, advantageously in the second heat exchanger.

3. The method according to claim 1, wherein at least a part of the first expanded fraction coming from the first turbine is cooled by heat exchange with at least a part of the first headstream, advantageously in the second heat exchanger, before injection into the first column.

4. The method according to claim 1, wherein the second fraction of the feed stream is cooled and is partially condensed advantageously in the first heat exchanger, the second cooled and partially condensed fraction being injected into a second separating flask, the third headstream coming from the second separating flask being at least partially injected into the second dynamic expansion turbine.

5. The method according to claim 4, wherein the third bottoms stream coming from the separating flask is expanded, and is heated, advantageously in the first heat exchanger, then is injected into the first column and/or into the second fractionating column.

6. The method according to claim 1, wherein a fraction coming from the first bottoms stream recovered from the first separating flask is injected into a liquid stream formed from the second fraction of the feed stream.

7. The method according to claim 1, wherein said method further comprises:
expansion, heating, and partial evaporation of the first bottoms stream coming from the first separating flask;
injection of the first bottoms stream into a downstream separating flask to form a fourth bottoms stream and a fourth headstream, the fourth headstream being cooled, advantageously in the second heat exchanger, then being injected into the first column to form a second auxiliary feed stream.

8. The method according to claim 1, wherein said method further comprises:
injecting the second expanded fraction coming from the second dynamic expansion turbine into an auxiliary downstream separating flask to form a fifth gas headstream and a fifth liquid bottoms stream;
cooling the fifth gas headstream and injecting into the first column;
injecting the fifth liquid bottoms stream into the first column and/or into the second column.

9. The method according to claim 1, wherein the first bottoms stream coming from the first separating flask is heated in the first heat exchanger, before being injected into the second fractionating column.

10. The method according to claim 1, wherein said method further comprises:
separating the first headstream into a first turbine feed fraction, conveyed up to the first dynamic expansion turbine, and a column feed fraction that is injected into the second heat exchanger to form an auxiliary column feed stream;
injecting the auxiliary column feed stream into the first column.

11. The method according to claim 1, wherein said method further comprises:
removing, in the first headstream, a secondary recompression fraction upstream of the first compressor;
passage of the secondary recompression fraction into a third compressor coupled to the second dynamic expansion turbine;
injecting the secondary compressed recompression fraction coming from the third compressor into the first heated headstream downstream of the first compressor.

12. The method according to claim 1, wherein the second compressor comprises a first compression stage, at least one second compression stage and a refrigerant inserted between the first compression stage and the second compression stage, the method comprising a step for the passage of the first compressed overhead stream coming from the first compressor successively in the first compression stage, the refrigerant, then the second compression stage.

13. The method according to claim 1, wherein said method further comprises:
injecting at least part of the second expanded fraction coming from the second dynamic expansion turbine into an auxiliary column;
recovering a third bottoms stream coming from the auxiliary column,
forming the second column feed stream from the third auxiliary column bottoms stream.

14. The method according to claim 13, wherein said method further comprises:
separating the feed stream into the first fraction of the feed stream, the second fraction of the feed stream, and a third fraction of the feed stream;
cooling the third fraction of the feed stream by heat exchange with at least part of the first headstream coming from the first column, advantageously in an upstream heat exchanger separate from the second heat exchanger, and
mixing the third fraction of the cooled feed stream in the first fraction of the cooled feed stream, before passage in the first separating flask.

15. The method according to claim 1, wherein said method further comprises:
passage of the first headstream into the first heat exchanger;
removal of an auxiliary expansion stream in the first headstream, after its passage in the first heat exchanger;
dynamic expansion of the auxiliary expansion stream in an auxiliary dynamic expansion turbine;
injection of the expanded stream coming from the auxiliary dynamic expansion turbine into the first headstream, before its passage in the first heat exchanger.

16. The method according to claim 1, wherein said method further comprises:
removing a recirculation stream in the first headstream or in a stream formed from the first headstream;
expansion and injection of the expanded recirculation stream in a stream circulating upstream of the first dynamic expansion turbine, advantageously in the first fraction of the first cooled feed stream or in the first turbine feed stream.

17. The method according to claim 1, wherein said method further comprises pumping the first bottoms stream and heating the first bottoms stream in the first heat exchanger before it is injected into the second fractionating column.

18. A piece of equipment for producing a $C_3^+$ hydrocarbon-rich cut and a methane-rich stream, from a feed stream containing hydrocarbons, the equipment comprising:
a first heat exchanger to partially cool and condense a first fraction of the feed stream to provide a first cooled fraction;
a first separating flask for receiving the first cooled fraction to form a first gas headstream and a first liquid bottoms stream;
a first dynamic expansion turbine for receiving at least part of the first gas headstream to provide a first expanded fraction;
a first column for receiving a first feed stream formed by at least a portion of the first expanded fraction coming from the first dynamic expansion turbine in a lower part of the first column and for receiving at least a part of first liquid bottoms stream to recover a first headstream and a first bottoms stream;
a second heat exchanger for heating at least part of the first headstream; and
a first compressor coupled to the first dynamic expansion turbine and a second compressor to compress the heated headstream so as to form the methane-rich stream;
a second fractionating column for receiving at least part of the first bottoms stream and at least a part of first liquid bottoms stream to recover a second headstream and a second bottoms stream that provides the $C_3^+$ hydrocarbon-rich cut;

wherein the first heat exchanger partially cools and condenses the second headstream;

a head separating flask for receiving the second partially condensed headstream to form a second gas headstream and a second liquid bottoms stream that is returned in reflux to the second fractionating column;

wherein the second heat exchanger partially cools and condenses the second gas headstream;

an expansion valve for expanding the second partially condensed gas headstream before the second partially condensed gas headstream is returned to the first column in reflux;

a second dynamic expansion turbine for receiving at least part of a second fraction of the feed stream to form a second expanded fraction; and wherein the second heat exchanger cools at least part of the second expanded fraction which forms a second feed stream to the first column.

19. A piece of equipment for producing a $C_3^+$ hydrocarbon-rich cut and a methane rich stream, from a feed stream containing hydrocarbons, the equipment comprising:

a first heat exchanger to partially cool and condense a first fraction of the feed stream to provide a first cooled fraction;

a first separating flask for receiving the first cooled fraction to form a first gas headstream and a first liquid bottoms stream;

a first dynamic expansion turbine for receiving at least part of the first gas headstream to provide a first expanded fraction;

a first column for receiving a first feed stream formed by at least a portion of the first expanded fraction coming from the first dynamic expansion turbine in a lower part of the first column and for receiving at least a part of first liquid bottoms stream to recover a first headstream and a first bottoms stream;

a second heat exchanger for heating at least part of the first headstream; and a first compressor coupled to the first dynamic expansion turbine and a second compressor to compress the heated headstream so as to form the methane-rich stream;

a second fractionating column for receiving at least part of the first bottoms stream and at least a part of first liquid bottoms stream to recover a second headstream and a second bottoms stream that provides the $C_3^+$ hydrocarbon-rich cut;

wherein the first heat exchanger partially cools and condenses the second headstream;

a head separating flask for receiving the second partially condensed headstream to form a second gas headstream and a second liquid bottoms stream that is returned in reflux to the second fractionating column;

wherein the second heat exchanger partially cools and condenses the second gas headstream;

an expansion valve for expanding the second partially condensed gas headstream before the second partially condensed gas headstream is returned to the first column in reflux;

a second dynamic expansion turbine for receiving at least part of a second fraction of the feed stream to form a second expanded fraction; and a downstream heat exchanger cools at least part of the second expanded fraction by heat exchange with at least part of the first headstream coming from the first column, which forms a second feed stream to the first column.

20. The equipment according to claim 19, further comprising:

an auxiliary column;

for receiving at least part of the second expanded fraction from the second dynamic expansion turbine, to provide a third bottoms stream that is utilized as the second feed stream of the first column.

* * * * *